United States Patent
Casey et al.

(10) Patent No.: US 6,171,582 B1
(45) Date of Patent: Jan. 9, 2001

(54) METHOD OF REDUCING OR PREVENTING MALODOUR

(75) Inventors: John Casey, Vlaardingen (NL); Alexander Gordon James, Bedford (GB); Jayne Elizabeth Ellis, Bedford (GB); Gary Mycock, Bedford (GB); David Taylor, Merseyside (GB)

(73) Assignee: Unilever Home & Personal Care USA, Division of Conopco, Inc., Chicago, IL (US)

( * ) Notice: Under 35 U.S.C. 154(b), the term of this patent shall be extended for 0 days.

(21) Appl. No.: 09/348,609

(22) Filed: Jul. 6, 1999

(30) Foreign Application Priority Data

Jul. 7, 1998 (GB) .................................................. 9814732

(51) Int. Cl.⁷ ................................ A61K 7/32; A61K 7/00
(52) U.S. Cl. ........................... 424/65; 424/400; 424/401
(58) Field of Search ................................ 424/65, 400, 401

(56) References Cited

U.S. PATENT DOCUMENTS

| | | | |
|---|---|---|---|
| 4,005,189 | * 1/1977 | Reese et al. | 424/65 |
| 4,089,942 | 5/1978 | Bore' et al. | 424/47 |
| 4,356,190 | 10/1982 | Kraskin | 424/319 |
| 5,433,943 | 7/1995 | Osipow et al. | 424/65 |
| 5,641,475 | 6/1997 | Yu et al. | 424/65 |
| 5,683,682 | 11/1997 | Betts | 424/65 |

FOREIGN PATENT DOCUMENTS

| | | |
|---|---|---|
| 43 21 753 | 1/1995 | (DE) . |
| 196 20 644 | 11/1997 | (DE) . |
| 197 40 879 | 4/1999 | (DE) . |
| 0636359 | 2/1995 | (EP) . |
| 0750903 | 1/1997 | (EP) . |
| 002120395 | 10/1997 | (JP) . |
| 94/07837 | 4/1994 | (WO) . |
| 97/44006 | 11/1997 | (WO) . |

OTHER PUBLICATIONS

International Search Report Application No. PCT/GB 99/02055 mailed Nov. 10. 1999.
Copending application: Applicant: Casey et al. Serial No.: 09/348,606 Filed: Jul. 6, 1999 For: Cosmetic Composition.
Copending application: Applicant: Casey et al. Serial No. 09/348,607 Filed: Jul. 6, 1999 For: Method of Reducing or Preventing Malodour.
Copending application: Applicant: Casey et al. Serial No.: 09/348,608 Filed: Jul. 6, 1999 For: Method of Reducing or Preventing Malodour.

* cited by examiner

Primary Examiner—Shelley A. Dodson
(74) Attorney, Agent, or Firm—Matthew Boxer

(57) ABSTRACT

Cosmetic method for reducing or preventing body malodor by topically applying to human skin an active agent capable of inactivating body malodor-causing microorganisms comprising corynebacteria, characterised in that the agent is capable of inactivating, of the corynebacteria, only those corynebacteria capable of catabolising fatty acids.

3 Claims, No Drawings

METHOD OF REDUCING OR PREVENTING MALODOUR

This invention relates to a cosmetic method for reducing or preventing body malodour.

In particular, it relates to a cosmetic method for reducing or preventing body malodour by topically applying to human skin an active agent capable of inactivating body malodour causing micro-organisms comprising corynebacteria, characterised in that the agent is capable of selectively inactivating, of the corynebacteria, only those corynebacteria capable of catabolising fatty acids.

It is well known that freshly secreted sweat is sterile and that body malodour is the result of biotransformation of the sweat by micro-organisms living on the surface of the skin to produce volatile odoriferous compounds.

There are three types of composition routinely used to combat body malodour: perfumes, antiperspirants and deodorants.

Perfumes are designed simply to mask body malodour.

Antiperspirant actives work by blocking the sweat glands thereby reducing perspiration. However, even the best cosmetically acceptable antiperspirant actives rarely reduce sweat production by more than 50%.

Deodorant actives, on the other hand, are designed to reduce the population of micro-organisms living on the surface of the skin. Typical deodorants include ethanol and triclosan (2,4,4'-trichloro,2'-hydroxy-diphenyl ether) which is a well known antimicrobial agent. The skin is host to a number of microorganisms some of which are beneficial and others which are not. The use of common deodorant actives results in the indiscriminate killing of most of the skin's natural microflora including the beneficial species. This is considered an undesirable side effect of such deodorant formulations.

Many disclosures describe compositions comprising anti-microbials which are designed to eliminate malodour by reducing the microfloral population.

WO 95/16429 (Henkel) describes deodorant compositions comprising fat soluble partial esters of hydroxy carboxylic acids.

WO 95/07069, WO 91/11988 and WO 91/05541 (all Gillette) describe deodorant compositions comprising inhibitors of pyridoxal phosphate dependent amino acid lyase.

WO 94/14934 (Unilever) describes a method for reducing the perceptibility of an odoriferous substance using an antibody or antibody fragment. Such antibodies could be used in deodorant compositions.

WO 93/07853 (Monell) describes the use of mimics of the odoriferous 3-methyl-2-hexenoic acid to reduce body malodour. DD 29 39 58 (Medezinische Fakultaet (Charité) der Humboldt Universitaet zu Berlin) describes the use of lipoxygenase inhibitors to act biochemically to reduce sweat production or to inhibit, to various degrees, the action of skin bacteria or their enzymes on the decomposition of sweat to form unpleasant-smelling substances.

DE 43 43 265 (Henkel) describes deodorant compositions comprising saturated dioic acid (C3–C10) esters. The active inhibits a sweat decomposing esterase and the compositions are said to not disturb the skin's natural microflora.

DE 43 43 264 (Henkel) describes the use of lipid-soluble partial esters of hydroxy carboxylic acids in deodorant compositions.

Coryneform bacteria are a group of bacteria including Actinomyces, Arachnia, Arcanobacterium, Arthobacter, Bacterionema, Bifidobacterium, Brevibacterium, Cellulomonas, Corynebacterium, Eyrsipelothrix, Eubacterium, Kurthia, Listeria, Mycobacterium, Nocardia, Oerskovia, Propionibacterium, Rhodococcus and Rothia. (The Skin Microflora and Microbial Skin Disease, W C Noble. Cambridge University Press 1992). Coryneform bacteria are believed to contribute to the formation of body malodour.

We have now found that the Corynebacterium genus can be subdivided into 2 subgroups according to ability to catabolise fatty acids and that one of these subgroups, hereinafter referred to as "corynebacteria A", which is capable of catabolising fatty acids, contributes strongly to the formation of body malodour, in particular axillary malodour, while the other subgroup, hereinafter referred to as "corynebacteria B", which catabolises fatty acids much less so or not at all, contributes much less or even not substantially to malodour formation. We also found that it is possible to selectively inactivate corynebacteria A as compared to corynebacteria B.

We further found that on average there is a difference between the axillary microflora of males and females and in the typical strength and nature of male and female malodour, in particular axillary malodour. Whereas for females corynebacteria A tend to comprise a smaller proportion of the axillary microflora, we found that for many males malodour formation is largely caused by corynebacteria A.

By corynebacteria is meant all strains of the Corynebacterium genus.

The deodorants available on the market tend to be insufficiently effective or substantially reduce the numbers of all bacteria in the microflora indiscriminately. The present invention offers the opportunity to provide deodorant products which for many females will substantially reduce malodour formation while inactivating only a minor portion of the microflora. For many males malodour formation can be substantially reduced or even largely eliminated while inactivating only one subgroup of the microflora, the corynebacteria A.

Furthermore, we found a range of preferred specific active ingredients for selectively inactivating corynebacteria A, while leaving other bacteria, notably corynebacteria B much less affected or even not notably affected at all.

Accordingly, the invention provides a cosmetic method for reducing or preventing body malodour by topically applying to human skin an active agent capable of inactivating body malodour causing micro-organisms comprising corynebacteria, characterised in that the agent is capable of selectively inactivating, of the corynebacteria, only those corynebacteria capable of catabolising fatty acids.

The invention also provides the use of an active agent capable of inactivating body malodour causing microorganisms comprising corynebacteria in the manufacture of a cosmetic composition for reducing or preventing body malodour, characterised in that the agent is capable of selectively inactivating, of the corynebacteria, only those corynebacteria capable of catabolising fatty acids.

According to the invention, inactivating microorganisms is any sub-lethal effect resulting in a reduction or elimination of the production of odoriferous metabolites, e.g. by modification of bacterial metabolism, in particular, fatty acid metabolism.

Sub-lethal means a significant inhibition of metabolism, e.g. pentadecanoic acid utilisation ($\geq 60\%$ inhibition), without concomitant reductions in cell viability ($\leq 1 \log_{10}$ CFU/ml reduction) and glucose utilisation ($\leq 10\%$ reduction).

By selectively inactivating of the corynebacteria only those corynebacteria capable of metabolising fatty acids is meant inactivating corynebacteria A to a significantly higher degree than corynebacteria B. Preferably it means inactivating corynebacteria A to a significantly higher degree than the majority, preferably at least 75%, more preferably at least 90% of bacteria other than corynebacteria A constituting the skin microflora.

The active employed in the present invention can suitably be an agent which is more active against corynebacteria A than against corynebacteria B. Preferably the agent is more active against corynebacteria A than against the majority of other bacteria constituting the skin microflora including corynebacteria B.

The following is an inexhaustive list of active agents according to the invention:

1. inactivating agents targeted to corynebacteria A by antibodies, antibody fragments and hydrophobic proteins; and
2. agents capable of modifying the metabolism, in particular, fatty acid metabolism, of malodour producing microorganisms comprising corynebacteria, but, of corynebacteria, only those corynebacteria capable of catabolising fatty acids resulting in a reduction or elimination of the production of odoriferous compounds.

It should be noted that active agents according to the invention do not include perfume components.

By perfume component is meant an ingredient which is added to a perfume to contribute to the olfactory properties of the perfume.

By perfume is meant a mixture of perfume components, and optionally a suitable diluent, which is added to a product to provide it with a pleasing fragrance.

1. Agents targeted with antibodies or hydrophobic proteins:

By antibody is meant any complete antibody or a fragment thereof, which has a selective affinity to corynebacteria A.

Antibodies or antibody fragments can be employed to deliver active agents to target sites, with provision for binding to those target sites. In the invention herein, the target sites are cell-surface antigens of Corynebacterium A species. The active agent may be connected to the antibody or antibody fragment by a variety of means, e.g. chemical conjugation.

Examples of hydrophobic proteins include oleosins.

By agent is meant any active agent according to the invention.

2. Examples of actives capable of inhibiting metabolism, in particular fatty acid metabolism, include:

fatty acids, which can be saturated or unsaturated and optionally can be substituted, in particular those containing from 6 to 24 carbon atoms, e.g. palmitic and stearic acids and also including: hydroxy fatty acids, e.g ricinoleic acid, and juniperic acid;

alkali metal alkyl sulphates, where alkyl is C8–20, e.g. sodium dodecyl sulphate, sodium 7-ethyl-2-methyl-4-undecyl sulphate, and sodium primary alkyl (C9–13) sulphates;

dicarboxylic acids, which may be saturated or unsaturated, e.g. C18:1 dioic acid, C18:2 dioic acid, and medium chain length saturated or unsaturated dioic acids, e.g. azelaic acid, suberic acid, sebacic acid, undecanoic acid, dodecanoic acid and mixtures thereof;

aryl/phenyl alcohols, e.g. benzyl alcohol, t-butylhydroquinone, pyrocatechol, 2-amino-4-nit: -ophenol, salicyl alcohol, 3-hydroxybenzyl alcohol, 2,3-dimethoxybenzyl alcohol, 2,4-dimethoxybenzyl alcohol, 3,5-dihydroxybenzyl alcohol, 3-hydroxy-4-methoxybenzyl alcohol, 2-hydroxy-3-methoxybenzyl alcohol, coniferyl alcohol and 4-hydroxy-3-methoxyphenethyl alcohol;

aryl/phenyl acids, e.g. gallic acid, benzoic acid, salicylic acid, cinnamic acid, 3-methoxycinnamic acid, 4-methoxycinnamic acid, 2-hydroxycinnamic acid, 3-hydroxycinnamic acid, 4-hydroxycinnamic acid, 4-methoxybenzenepropionic acid, 3,4-dihydroxybenzenepropionic acid, 4-hydroxybenzenepropionic acid, ferulic acid and 2-methoxycinnamic acid;

phenyl esters, e.g. benzyl cinnamate;

monoterpene derivatives, e.g. geranic acid;

osmotic agents, e.g. sodium chloride;

sterols, e.g. cholesterol, and ergosterol;

steroids, e.g. testosterone, and androstenedione;

flavonoids, e.g. naringenin, isosakuranetin, eriodictyol, and genistein;

steryl esters, e.g. amyrin cinnamate;

2,7-naphthalenediol, and oxyquinoline.

aryl/phenyl ketones, e.g. 4-hydroxy-3-methoxyphenylacetone and 4-(4-hydroxy-3-methoxyphenyl)-3-buten-2-one Two or more of the active agents described hereinbefore can be employed.

The active agent according to the present invention may preferably be employed in a composition which may be applied to human skin for the reduction or elimination of body malodour. Examples of products comprising an active agent according to the invention include antiperspirants, deodorants, shampoos, conditioners, skin cleansers, detergents, hair conditioners, sunscreens, sun tan lotions, skin conditioners, etc. It is to be understood that this list is not exhaustive with regard to suitable products comprising active agents according to the invention.

Typical deodorant compositions comprising an active agent according to the invention may also comprise other materials commonly found in underarm compositions such as deodorant or antiperspirant compositions, for example, cosmetically acceptable vehicles; deodorant actives; perfumes; antiperspirant actives; skin benefit agents; colours; water; humectants and other cosmetic adjuncts conventionally employed in such compositions. The use of such substances depends on the form of the composition which may be an aerosol, stick, roll-on, gel, lotion, cream, ointment, powder, suspension or soap.

The active agent may be used in an amount effective to inactivate, of corynebacteria, only those corynebacteria capable of catabolising fatty acids. Usually the active agent may be present in an amount ranging from 0.001 to 10% by weight of the composition, preferable from 0.01to 2%.

EXAMPLE 1

The demonstration of fatty acid catabolism in a particular bacterial strain was determined in vitro using the method given below:

The in vitro model system, reproducing fatty acid catabolism by axillary bacteria, consisted of 250 ml baffled shake flasks, to which were added 30 ml semi-synthetic medium (see below) supplemented with fatty acid substrate 2.0 mg/ml pentadecanoic acid) and non-fatty acid substrate (0.5–1.0 mg/ml glucose). This system was employed to evaluate selected potential deodorant actives (see below). Flasks were inoculated with fresh bacterial biomass, pregrown for 24 h in TSBT (see below), to give starting optical densities ($A_{590}$) of 1.0–2.0. Following inoculation, flasks were incubated aerobically at 35° C., with agitation (130 rpm), and analysed after 24 h. Culture viability/purity was determined by TVC analysis on TSAT plates (see below) following serial dilution in quarter-strength Ringers solution. Fatty acids were determined by capillary gas chromatography (GC) (see below). Residual glucose concentrations were measured with blood glucose test strips (BM-Test 1–44; Boehringer Mannheim) used in conjunction with a Refloflux™S glucose meter (Boehringer Mannheim).

Fatty acid levels in the flasks were determined by capillary GC analysis. Initially, 5.0 ml aliquots from each flask were rapidly transferred into universal tubes; an internal standard (1.0 mg/ml lauric acid) was added to each universal and the culture medium was acidified (pH ~2) by the addition of hydrochloric acid. Liquid-liquid extraction was then carried out using 2 vol (10 ml) ethyl acetate; organic and aqueous phases were resolved by centrifugation (2000 rpm, 3 min). 2.0 ml of each organic (upper) phase was then transferred to a sampling tube prior to analysis on a Perkin Elmer 8000 (Series 2) GC fitted with a 15 m×0.32 mm (internal diameter) FFAP (nitroterephalic acid modified PEG/siloxane copolymer) fused silica capillary column (film thickness 0.25 $\mu$m) (Quadrex). This column was attached to the split-splitless injector and flame ionisation detector (FID) of the GC; injector and detector temperatures were each 300° C. Carrier gas for the column was helium (6.0 psi), while hydrogen (17 psi) and air (23 psi) supplied the FID. The temperature programme for fatty acid analysis was 800C. (2 min); 80–250° C. (20° C./min); 250° C. (5 min). Sample size for injection was 0.5–1.0 $\mu$l. Fatty acid levels in the flasks were quantified by comparison of peak areas with known levels of both internal (lauric acid) and externally run (pentadecanoic acid) standards.

EXAMPLE 2

Demonstration of sub-lethal inactivation of fatty acid metabolism was performed with the following in vitro method. Prior to inoculation, flasks were supplemented with selected materials, at a range of concentrations, to determine their ability to sub-lethally inhibit fatty acid catabolism by corynebacteria A. Stock active solutions/emulsions were prepared in semi-synthetic medium (see below), supplemented with Gum Arabic (5.0 mg/ml); emulsions were formed by ultra-homogenisation at 24,000 rpm for ~1 min. At the end of each experiment, viability, fatty acid levels and residual glucose concentrations in the experimental flasks were compared to those in a control flask. Sub-lethal inhibition of fatty acid catabolism was defined as significant inhibition of pentadecanoic acid utilisation, without concomitant reductions in cell viability or glucose utilisation.

Composition of Tween-supplemented Tryptone soya broth/agar (TSBT, TSAT) used for growth/maintenance of axillary bacteria (g/l): Tryptone soya broth (30.0) (Merck), Yeast extract (10.0) (Beta Lab), Tween 80 (1.0) (Tween is a trade mark of ICI Speciality Chemicals), ±Agar (20.0). Composition of semi-synthetic medium used in laboratory systems simulating fatty acid catabolism by axillary bacteria (g/l): $KH_2PO_4$ (1.6), $(NH_4)_2HPO_4$ (5.0), $Na_2SO_4$ (0.38), Yeast Nitrogen Base (Difco) (3.35), Yeast Extract (0.5), Tween 80 (0.2), Triton X-100 (trademark of Union Carbide) (0.2), $MgCl_2.6H_2O$ (0.5), Glucose (0.5–1.0), Pentadecanoic acid (2.0).

The effect of azelaic acid and benzoic acid on viability, glucose (1.0 g/l initial concentration) and pentadecanoic acid (2.0 g/l initial concentration) utilisation, by corynebacteria A (NCIMB 40928) after 24 h incubation is presented in Table 1. Initial biomass levels in each assay were identical.

TABLE 1

| Active, g/l | TVC ($log_{10}$ CFU/ml) | Glucose utilisation (%) | Penta-decanoic acid utilisation (%) | Inhibition of fatty acid catabolism (%) |
|---|---|---|---|---|
| CONTROL | 9.12 | 100.0 | 100.0 | (0.0) |
| Azelaic acid | | | | |
| 1.0 | 8.97 | 100.0 | 93.2 | 6.8 |
| 2.5 | 8.34 | 100.0 | 32.8 | 67.2 |
| 5.0 | 7.60 | 90.0 | 2.7 | 97.3 |
| 10.0 | 5.30 | 10.0 | 0.0 | 100.0 |
| Benzoic acid | | | | |
| 1.0 | 9.05 | 100.0 | 100.0 | 0.0 |
| 2.5 | 8.36 | 100.0 | 29.7 | 70.3 |
| 5.0 | 8.15 | 90.0 | 17.0 | 83.0 |
| 10.0 | 5.78 | 20.0 | 0.0 | 100.0 |

The results in Table 1 clearly demonstrate that both azelaic acid, at a concentration of 2.5 mg/ml, and benzoic acid, at 2.5 and 5.0 mg/ml, sub-lethally inhibit fatty acid catabolism, i.e. inactivate corynebacteria A as defined in the invention.

EXAMPLE 3

The following is a typical formulation which comprises an agent capable of inactivating body malodour causing microorganisms comprising corynebacteria, characterised in that the agent is capable of inactivating, of the corynebacteria, only those corynebacteria capable of catabolising fatty acids.

It is made by a method common in the art.

TABLE 2

| Ingredient | Content % by weight |
|---|---|
| Ethanol | 56.5 |
| Benzyl alcohol | 1.00 |
| Isopropyl myristate | 1.0 |
| Fragrance | 1.5 |
| Propellant | 40.0 |

EXAMPLE 4

A further example of sub-lethal inactivation of corynebacteria A

The effect of ferulic acid on viability, glucose (0.5 mg/ml initial concentration) and pentadecanoic acid (2.0 mg/ml initial concentration) utilisation by Corynebacterium A sp. NCIMB 40928 after 24 h incubation is summarised in Table 3.

TABLE 3

| Active, mg/ml | TVC ($\log_{10}$ CFU/ml) | Glucose utilisation (%) | Pentadecanoic acid utilisation (%) | Inhibition of fatty acid catabolism (%) |
|---|---|---|---|---|
| Ferulic acid | | | | |
| 0.0 | 9.13 | 100 | 100 | 0 |
| 2.5 | 8.54 | 100 | 0 | 100 |
| 5.0 | 5.49 | 100 | 0 | 100 |

The results in Table 3 clearly demonstrate that ferulic acid, at a concentration of 2.5 mg/ml, sub-lethally inhibits fatty acid catabolism without concomitant reductions in cell viability and glucose utilisation, ie. inactivates corynebacteria A in accordance with the invention.

What is claimed is:

1. A method for reducing or preventing body malodour which comprises topically applying to human skin an active agent capable of inactivating, through a sub-lethal effect, body malodour-causing microorganisms comprising only those corynebacteria capable of catabolising fatty acids.

2. A method according to claim 1 wherein the active is a fatty acid containing 6 to 24 carbon atoms, an alkali metal alkyl sulphate containing from 8 to 20 carbon atoms, a saturated or unsaturated dicarboxylic acid containing at least 8 carbon atoms, a phenyl alcohol, a phenyl acid, a phenyl ester, a monoterpene derivative, an osmotic agent, a sterol, a steroid, a flavonoid, a steryl ester, naphthalene-2,7-diol or oxyquinoline.

3. A method according to claim 2 wherein the active agent is selected from the group consisting of ricinoleic acid, C18:1 dioic acid, salicylic acid, benzyl alcohol, benzoic acid, ferulic acid, naringenin, hydroxybenzyl alcohols, hydroxymethoxybenzyl alcohols, and dimethoxybenzyl alcohols.

* * * * *